United States Patent [19]

Mattern et al.

[11] Patent Number: 5,756,071
[45] Date of Patent: May 26, 1998

[54] METHOD FOR NASALLY ADMINISTERING AEROSOLS OF THERAPEUTIC AGENTS TO ENHANCE PENETRATION OF THE BLOOD BRAIN BARRIER

[75] Inventors: Claudia Mattern, Starnberg; Rudiger Hacker, Herrsching, both of Germany

[73] Assignee: Arrowdean Limited, Dublin, Ireland

[21] Appl. No.: 791,549

[22] Filed: Jan. 31, 1997

Related U.S. Application Data

[63] Continuation of Ser. No. 347,350, Dec. 27, 1994, abandoned.

[30] Foreign Application Priority Data

Jun. 3, 1992 [DE] Germany ............... 42 18 291.3

[51] Int. Cl.$^6$ ...................................... A61K 9/12
[52] U.S. Cl. ...................................... 424/45; 424/46
[58] Field of Search ...................... 424/45, 46, 434

[56] References Cited

U.S. PATENT DOCUMENTS 3,014,844  12/1961  Thiel ........................... 424/45

FOREIGN PATENT DOCUMENTS

| 0 160 501 | 11/1985 | European Pat. Off. |
| 6 033 | 5/1968 | France. |

*Primary Examiner*—Raj Bawa
*Attorney, Agent, or Firm*—Merchant, Gould, Smith, Edell, Welter & Schmidt, P.A.

[57] ABSTRACT

Described is a metering spray designed for pernasal application, the spray containing at least one sex hormone or at least one metabolic precursor of a sex hormone or at least one derivative of a sex hormone or combinations of these, excepting the precursors of testosterone, or at least one biogenic amine, with the exception of catecholamines.

3 Claims, No Drawings

METHOD FOR NASALLY ADMINISTERING AEROSOLS OF THERAPEUTIC AGENTS TO ENHANCE PENETRATION OF THE BLOOD BRAIN BARRIER

CROSS REFERENCE TO RELATED APPLICATION

This application is a file wrapper continuation of U.S. patent application Ser. No. 08/347,350, filed on Dec. 22, 1994, abandoned, and claims priority through PCT application no. PCT/DE93/00442 filed May 17, 1993 to German national application no. P 42 18 291.3 filed Jun. 3, 1992.

BACKGROUND OF THE INVENTION

1. Field of the Invention

The invention relates to novel dosing or metering sprays for pernasal application.

2. Description of the Prior Art

Numerous pharmaceutical substances have their pharmacodynamic action in the central nervous system. Thus, the latest research has revealed that sex hormones and their derivatives in part reveal unexpected, positive side-effects in the central nervous system, particularly in that the general psychophysiological stressability of the patient perceptibly rises. Other substances, such as certain biogenic amines have a therapeutic activity which is directly dependent on a facilitated access to the central nervous system. This is a decisive action prerequisite e.g. for medicaments for treating Parkinson's disease, such as e.g. dopamine, dopamine derivatives, NADH or NADPH.

If, as a result of their chemical properties active substances undergo modifications in the gastrointestinal tract due to the varying pH-conditions and enzymatic processes (such as e.g. most biogenic amines) or if they are only water-soluble to a limited extent (such as sex hormones) hitherto complicated galenic administration forms have been necessary, or it has been necessary to use the parenteral administration form, which stresses the patient and requires the calling in of the doctor.

EP-A-272 097 points out that progesterone from the nasal cavity is absorbed in such a way that the resulting blood levels are virtually equivalent to intravenous administration.

EP-A-160 501 discloses an intranasal formulation for catecholamine, which is suspended in fatty acid or ester and emulsified with polyoxyethylene.

From the not previously published patent application P 42 14 053.3 of the same application is known a dosing spray for the application of testosterone precursors.

The problem of the present invention is to provide an administration form, which favours the access of certain active substances to the central nervous system and therefore permits a reduction in the single dose and/or supply of active substances, which cannot be perorally supplied for the indicated reasons.

SUMMARY OF THE INVENTION

According to the invention this problem is solved by a dosing spray having a content of at least one sex hormone or at least one metabolic precursor of a sex hormone or a combination thereof, excepting the precursors of testoserone, or at least one biogenic amine, excepting catecholamines.

Particular preference is given to a dosing spray having a content of dopamine, dopamine derivative, NADH, NADPH or a combination thereof.

The preferred dosage is between 2 and 20 mg of active substance per spray stroke.

DETAILED DESCRIPTION OF THE INVENTION

Further features and advantages of the invention can be gathered from the following description of a preferred embodiment.

Application of testoserone by means of a dosing spray

The advantages of administration by means of a dosing spray were tested in comparison with the oral administration of testosterone.

The peroral supply of 100 mg of testosterone by means of a capsule increased the blood level from a starting concentration between 32.5 and 37.5 nmole/l to values between 45 and 50 nmole/l. The concentration maximum was reached 30 min. after administration, but was subject to marked individual fluctuations.

The profile of the steroids eliminated in the urine reacted very strongly and there were e.g. increases in the testosterone/epitestosterone quotient starting from the normal range between 0.9 and 2.8 to values up to 60.

The blood level kinetics individually varied widely and in part 60 to 90 min following administration the initial values were again reached.

When testosterone was administered by means of a nasal spray in order to achieve the same rise in the blood level only a dose of 7 or 14 mg per application was needed.

Application was much better to control. The blood concentration rises in individual test persons in stable manner were 1.5 to 2 times the individual starting concentrations. The time during which the maximum blood concentration was reached was clearly reduced to 15 to max 90 min.

The disturbances in the urine steroid profile were clearly reduced and the testosterone/epitestosterone quotient only rose to values between 15 and 20 and was normalized within 24 hours.

Following pernasal application all the test persons mentioned an improved psychophysiological stressability. This effect was not observed with peroral administration. It is attributed to the preferred influencing of the central nervous steroid receptors, probably caused by easier passage through the blood-brain barrier in pernasal application.

Application of anti-Parkinsons's disease agents

For therapeutics used in the treatment of Parkinson's disease, an essential action prerequisite is the passage through the blood-brain barrier.

Building up on the aforementioned results NADH was pernasally applied in a pilot study. In pilot studies with parenteral administration of 5 to 10 mg of NADH (infusion over 30 min) it was found that the tremor frequency significantly decreased and both the mobility and target accuracy or aim of the movements is improved. For the same dosage intranasal NADH application revealed the same action. Thus, it is possible to avoid the risky, stressing intravenous infusion and instead to obtain by means of the dosing spray an application which is more appropriate for the disease and age.

In the case of pernasal application the active substance can also be available in powder form. As a result of the spray stroke there is a very fine distribution in the vicinity of the nose and nasal sinuses, which favours resorption over a large surface. The galenic formulation as a dry substance eliminates the problems associated with the keeping quality and stability of the active substance. The preferred administration as a nasal spray is consequently particularly suitable for outpatient therapy of Parkinson's disease.

The features of the invention disclosed in the description and claims can be essential to the implementation of the invention in its various embodiments either singly or in random combination.

We claim:

1. A method for facilitating the passage of testosterone through the blood-brain barrier, the method comprising the step of administering nasally as a aerosol a dose of about 7 mg to about 14 mg testosterone using a metering spray designed for pernasal application; wherein the nasal administration results in a higher concentration of testosterone in the central nervous system that when the same dose is administered orally.

2. A method for facilitating the passage of dopamine, L-DOPA, NADH, NADPH or combinations thereof through the blood-brain barrier, the method comprising the step of administering nasally as an aerosol a dose of about 2 mg to about 20 mg of dopamine, L-DOPA, NADPH, or a dose of about 5 mg to about 10 mg NADH, or a combination thereof using a metering spray designed for pernasal application; wherein the nasal administration results in a higher concentration of dopamine, L-DOPA, NADH, NADPH or a combination thereof in the central nervous system than when the same dose is administered orally.

3. The method according to claim 2, wherein the dose of NADH is about 5 mg to about 10 mg.

* * * * *